US011213315B2

(12) United States Patent
Kincaid

(10) Patent No.: US 11,213,315 B2
(45) Date of Patent: Jan. 4, 2022

(54) METHOD AND APPARATUS FOR A MEDICAL GUIDANCE DEVICE

(71) Applicant: Canon USA Inc., Melville, NY (US)

(72) Inventor: Matthew Michael Kincaid, Medford, MA (US)

(73) Assignee: Canon U.S.A., Inc., Melville, NY (US)

( * ) Notice: Subject to any disclaimer, the term of this patent is extended or adjusted under 35 U.S.C. 154(b) by 214 days.

(21) Appl. No.: 16/351,288

(22) Filed: Mar. 12, 2019

(65) Prior Publication Data

US 2019/0282263 A1      Sep. 19, 2019

Related U.S. Application Data

(60) Provisional application No. 62/643,961, filed on Mar. 16, 2018.

(51) Int. Cl.
| | |
|---|---|
| *A61B 17/34* | (2006.01) |
| *A61B 34/20* | (2016.01) |
| *A61B 90/11* | (2016.01) |
| *A61M 25/02* | (2006.01) |
| *A61B 90/00* | (2016.01) |

(52) U.S. Cl.
CPC .......... *A61B 17/3403* (2013.01); *A61B 34/20* (2016.02); *A61B 90/11* (2016.02); *A61B 2017/3407* (2013.01); *A61B 2017/3409* (2013.01); *A61B 2090/067* (2016.02); *A61B 2090/0807* (2016.02); *A61M 25/02* (2013.01)

(58) Field of Classification Search
CPC ....... A61B 19/20; A61B 19/22; A61B 19/201; A61B 19/203; A61B 19/5244; A61B 2017/3407; A61B 17/3403; A61B 34/20; A61M 25/02
See application file for complete search history.

(56) References Cited

U.S. PATENT DOCUMENTS

| | | | |
|---|---|---|---|
| 8,308,740 B2 | 11/2012 | Tolley et al. | |
| 8,790,311 B2 | 7/2014 | Gyrn | |
| 8,845,655 B2 * | 9/2014 | Henderson | ............. A61B 34/20 606/130 |
| 9,222,996 B2 | 12/2015 | Fujimoto et al. | |
| 9,877,787 B2 * | 1/2018 | Brabrand | ........... A61B 17/3403 |
| 2004/0260312 A1 | 12/2004 | Magnusson et al. | |
| 2008/0200798 A1 | 8/2008 | Eklund et al. | |
| 2012/0190970 A1 | 7/2012 | Velusamy et al. | |
| 2014/0336670 A1 | 11/2014 | Brabrand et al. | |
| 2016/0367789 A1 | 12/2016 | Beran | |

\* cited by examiner

*Primary Examiner* — Vi X Nguyen
(74) *Attorney, Agent, or Firm* — Canon U.S.A., Inc. IP Division

(57) ABSTRACT

Medical guidance device capable of improving precision and accuracy of medical surgery by ensuring accurate and consistent placement of the medical guidance device, as well as communication with surgery planning software and/or three-dimensional spatial software to determine insertion of the needle into the patient.

8 Claims, 5 Drawing Sheets

METHOD AND APPARATUS FOR A MEDICAL GUIDANCE DEVICE

CROSS REFERENCE TO RELATED PATENT APPLICATIONS

This application claims priority from U.S. Provisional Patent Application No. 62/643,961 filed on Mar. 16, 2018, in the United States Patent and Trademark Office, the disclosure of which is incorporated herein in its entirety by reference.

FIELD OF THE DISCLOSURE

The present disclosure relates generally to apparatus and methods for securing a medical guidance device to a subject, and, more particularly, to a medical guidance device for a needle, capable of adaptation and secure adhesion to various surface shapes on a subject.

BACKGROUND OF THE DISCLOSURE

Accurate and precise manipulation and orientation of medical tools is a critical factor in the successful use of these tools in surgical procedures. In particular, the accurate and precise orientation of a medical tool is especially critical in the insertion of a needle-like tool according to plan based on medical images, such as computed tomography (CT) and Magnetic Resonance Imaging (MRI) in percutaneous interventions.

The general purpose of any needle guidance device is to direct the needle onto a path passing precisely through a selected insertion point to the target location within the patient's anatomy. This objective involves limiting the position and orientation to one azimuthal angle and one angle of elevation with respect to a selected insertion point upon the patient's skin surface. Selection of an insertion point, and both azimuthal and elevation angles, defines the needle trajectory into the patient's anatomy. The needle is able to slide axially along the chosen trajectory, to the desired depth.

There are examples of needle guidance devices currently available on the market that incorporate adhesive mounts to attach to the patient's skin, and are adjustable so that the physician can choose a needle trajectory within some range. By way of example, United States Patent Publication No. 2014/0336670, and United States Patent Publication No. 2008/0200798, both disclose needle guidance devices that claim to achieve these objectives. Both devices provide a means to set a needle trajectory and claim to support the needle during partial insertions, and both devices have an adhesive layer under the base of the device to adhere the device to the patient skin surface.

However, in existing guidance devices, the trajectory is planned in relation to the target point and translated to the device by the clinician. The need for stability and near immobility of the guidance device on the patient is not addressed. In addition, the mounting systems taught assume a flat surface, which cannot be mounted on various locations on the patient's anatomy that may be curvaceous, may have significant compliance or softness, or may be located near obstacles such as the CT bed or the CT bore. In all instances, there needs to be a mounting solution that provides sufficient mounting stability, while allowing for adaptability to accommodate a subject, thus ensuring the accuracy and stability of the medical tool being inserted.

In addition, the onset of computer communication and guidance, which is used in combination with these devices, are adding additional technology to these relatively simple devices, enabling things like automatic registration between the physical world and CT/MRI planning software, or direct measurement of the intended trajectory using encoders. With this added complexity the need for additional precision and stability in the device, as well as a mounting system that is securely mounted to the patient, is highly desirable and increases efficacy. This added complexity may also increase the device size and weight, which may make stable and secure mounting of the device to the patient even more germane.

Accordingly, it is particularly beneficial to disclose a medical guidance device and method addressing these shortcomings, and advancing the technology to yield a stable and secure method and device, allowing for more accurate and precise mounting of the device with respect to the patient, thus leading to efficient use of CT/MRI planning software or trajectory using encoders to determine insertion of the needle into the patient.

SUMMARY

The present disclosure teaches a medical guiding device and methods for utilizing a medical guidance device. The medical guidance device has a base designed to guide a medical device into a subject's anatomy, and at least three resilient tabs each attached to the base and each extending distally from the base to provide support to the medical guidance device. The base is configured to allow for adjustment of the medical device to a specific and desired angle with respect to a patient's anatomy and the at least three tabs are attach to the patient's anatomy to provide the support needed to keep the base in place, such that the specific and desired angle of incidence for the medical device is kept stable. The at least three tabs are rotatable in a single axis to help conform to various shapes of a patient's anatomy, while providing stable support to the base.

In various embodiments of the subject disclosure, the axis of rotation of any one of the at least three tabs is in the axial direction with respect to the base.

In yet other embodiments, the medical guidance device may be configured to allow for additional tabs and/or reconfiguration of existing tabs.

In other embodiment, the medical guidance device incorporates adhesive for removably attaching each of at least three tabs is to the patient's anatomy.

In other embodiments, the subject medical guidance device utilizes reconfigurable tabs for each of at least three tabs, wherein the tabs may vary in shape and size.

In yet other embodiments, the medical guidance device further comprises an adhesive on the body for removably attaching the body to the patient's anatomy.

In various embodiment of the subject disclosure, the medical guidance device further comprises a support member attached to the base near a first end of the support member, and to one of the at least three tabs near a second end of the support member, wherein the support member provides support to one of the at least three tabs with respect to the base.

In other contemplated embodiment of the medical guidance device, the support member further comprises a releasable locking-adjustment mechanism. In addition, the support member may be hingedly attached to one of the at least three tabs near the second end of the support member, allowing for rotation in one axis.

In addition, the subject disclosure also discloses methods for guiding a medical device, the method comprising providing a medical guiding device having a base configured to guide a medical device and at least three tabs releasable attached to the base and extending distally from the base, wherein each of the at least three tabs are attach to the patient's anatomy, and each of the at least three tabs are rotatable in a single axis, the method further comprising attaching the medical guidance device to the patient's anatomy, followed by adjusting the medical guidance device to orient the medical device as desired, and treating the patient with the medical device.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Figure 1:
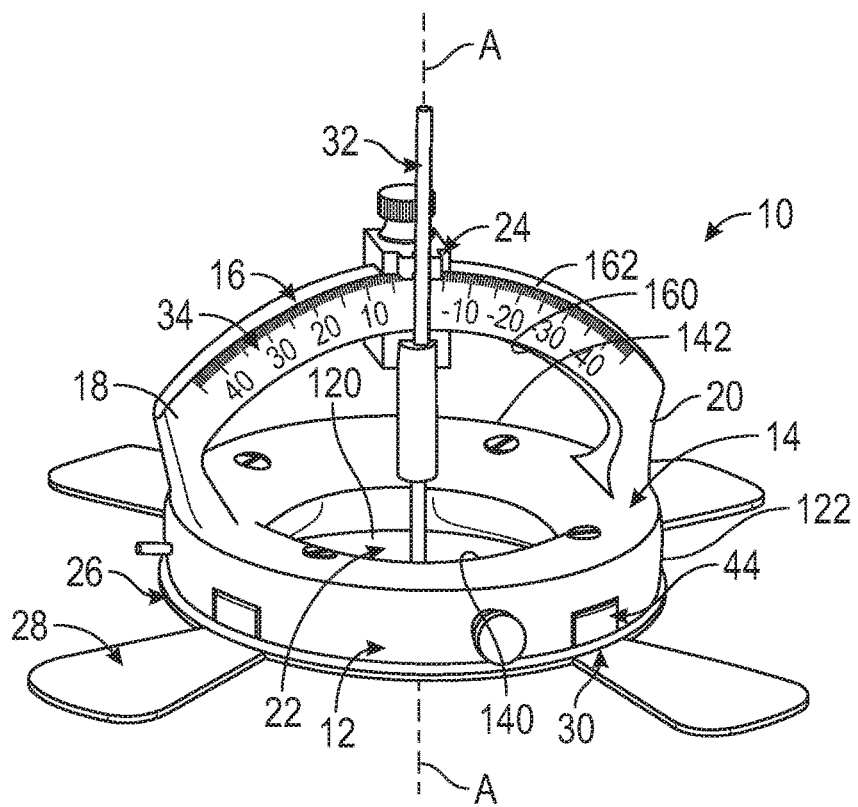
FIG. 1 is a perspective view of a medical guidance device, according to one or more embodiments of the present subject matter.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

The present disclosure details a medical device capable of stable guidance of a needle, syringe, probe, pick or speedles (collectively referred to herein as "needle") into and through the anatomy of a patient. More specifically, the subject medical guidance device contains an adjustable needle holder/guide capable of manipulation to orient the desired angle and trajectory of entry for a needle into a patient's anatomy, while ensuring the needle does not diverge from the desired angle and trajectory of entry while being used.

Figure 2:
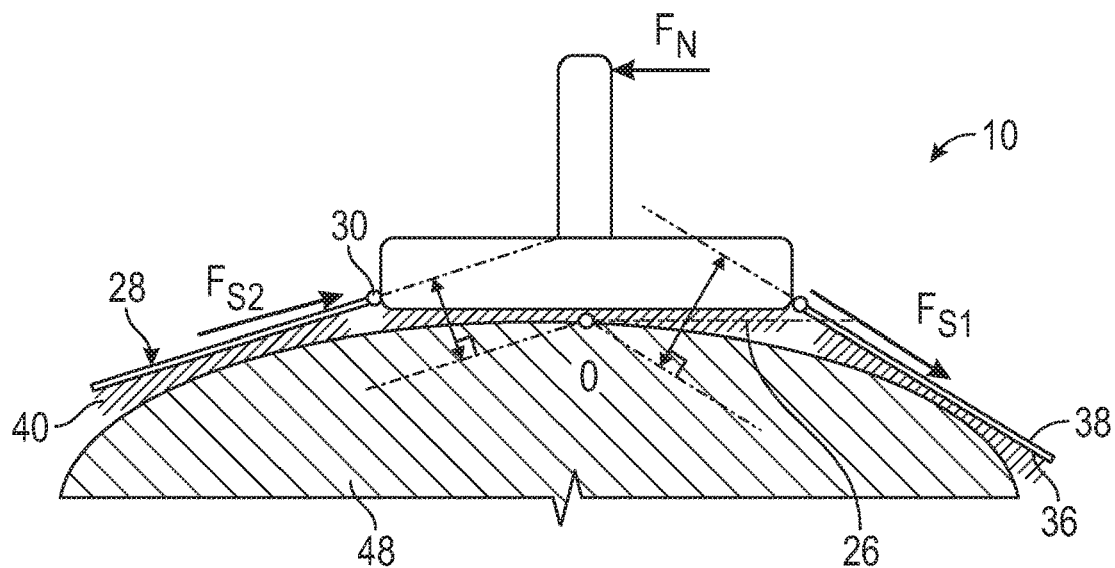
FIG. 2 is a side perspective of a medical guidance device, according to one or more embodiments of the present subject matter.
Figure 3:
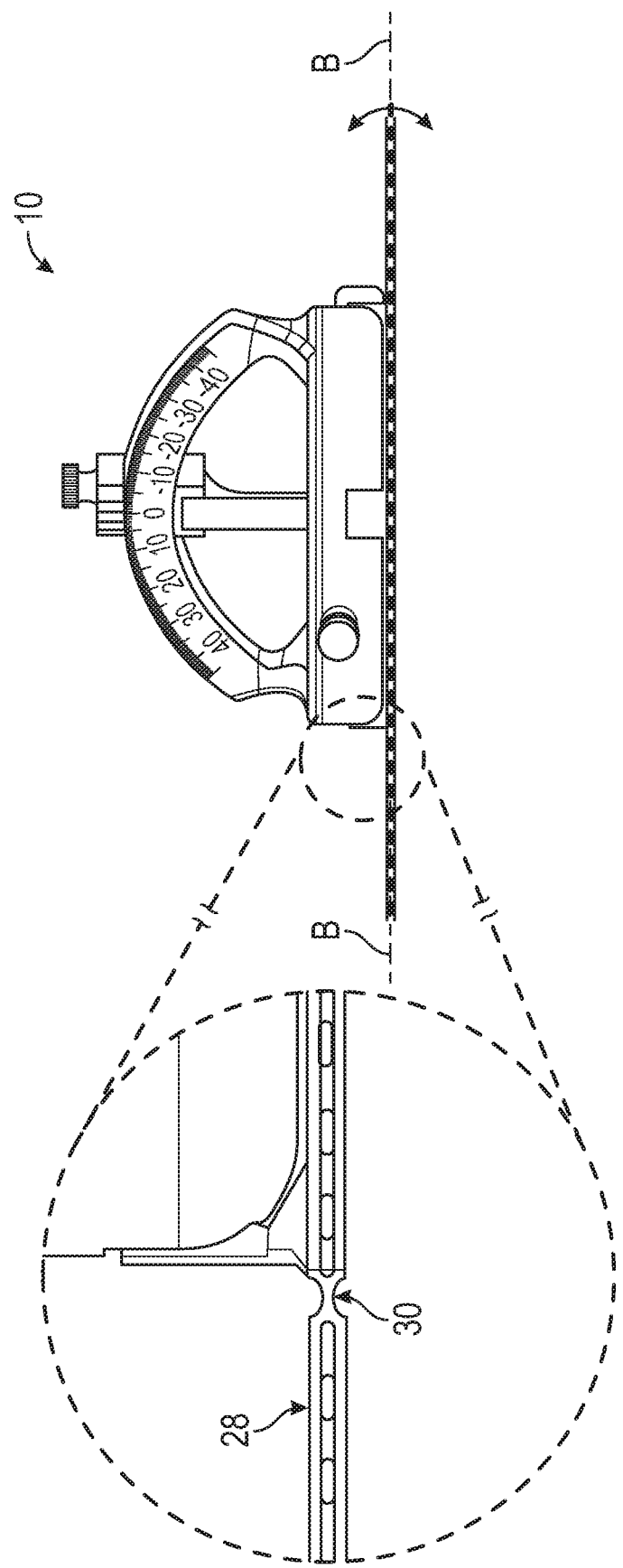
FIG. 3 provides a side perspective view of a medical guidance device, with a exploded view of one or more aspect of the medical guidance device, according to one or more embodiments of the present subject matter.

FIGS. 1, 2 and 3 provide various views of a medical guidance device 10, having a base plate 12 having an inner diameter 120 and an outer diameter 122, wherein the base plate 12 is configured to be in contact with patient's anatomy 48 (See FIG. 2), and a ring frame 14 rotatably coupled to the base plate 12. The ring frame 14 lies substantially parallel to the base plate 12 (and subsequent patient's anatomy), and is rotatable in a single axis about the vertical axis "A". The ring frame 14 has an inner diameter 140 and an outer diameter 142. The medical guidance device 10 further comprises an arc shaped guide 16 attached to the ring frame 14. As the arc shaped guide 16 is attached to the ring frame 14, the arc shaped guide 16 is also subject to rotation about the vertical axis "A" when the ring frame 14 is rotated. The arc shaped guide 16 attached to the ring frame 14 at a first end 18 and a second end 20, creating the 'arc' shape of the arc shaped guide 16. The arc shaped guide 16 also has an inner diameter 160 and an outer diameter 162.

The medical guidance device 10 provides a central opening 22, created by the arc shaped guide 16 inner diameter 160 and the base plate 12 and ring frame 14 inner diameters 120 and 14o, respectively, wherein the central opening 22 allows for access to the patient when the device 10 is removably attached to the patient's anatomy 48.

The arc shaped guide 16 further includes a needle guide 24, adjustably configured to the arc shaped guide 16, capable of guiding a needle 32 into the patient's anatomy 48. The needle guide 24 is configured to allow for rotation (and/or translation along the arc) of the needle guide 24, and accompanying needle 32, on the arc shaped guide 16, such that the angle of needle 32 entry into the patient's anatomy 48 may be adjusted as desired. The arc shape guide 16 may further include one or more reference markers 34 for aiding in adjusting the needle guide 24 to the desired angle. In addition, the needle guide 24 may be removable, with or without the needle 32 attached, from the arc shaped guide 16. As depicted in FIG. 1, the needle guide 24 is configured to be adjustable on the arc shaped guide 16, such that the point of entry of the needle 32 into the patient's anatomy 48 remains substantially the same, irrespective of the adjusted angle of entry for the needle 32. That is, as the angle of entry for the needle 32 is adjusted by adjusting the needle guide 24 on the arc shaped guide 16, the point of entry for the needle 32 into the patient's anatomy 48 remains substantially the same.

Furthermore, the medical guidance device 10 includes at least three rigid tabs 28, which are each removably attached to the base plate 12. The rigid tabs 28 consist of a rigid body having a ventral surface 36 and an opposing dorsal surface 38. The ventral surface 36 is configured for attachment to the surface of the patient's anatomy 48, and may include an adhesive or bonding agent 40 to removably and securely adhere to the patient's anatomy 48. The rigid tab 28 may comprise a clasp 44 (See FIG. 4), found at one end of the rigid tab 28, which may be removably matted to a cavity 46 found on the base plate 12. The clasp 44 is configured to partially or completely enter the cavity 46, thus attaching the rigid tab 28 to the base plate 12. The rigid tab 28 further comprises a hinge joint 30 configured about the clasp 44 of the rigid tab 28 to the base plate 12. The hinge joint 30 is constructed to allow for rotation of the rigid tab 28 about the horizontal axis "B" with respect to the base plate 12 for each rigid tab 28 (See FIG. 3). The hinge joint 30 is configured to allow for rotation of the rigid tab 28 about the horizontal axis "B", while retaining strength and integrity in the axial direction. Furthermore, the combination of at least three rigid tabs 28, each restricted to rotation of the rigid tab 28 about the horizontal axis "B" with respect to the base plate 12, work in unison to eliminate movement of the medical guidance device 10, once the rigid tabs 28 have been adhered to the patient's anatomy 48. In various other embodiments, one or more rigid tabs 28 may be affixed to the base plate 12 and/or ring frame 14.

The base plate 12 may be configured with a multitude of cavities 46 (See FIG. 4), allowing for adaptive attachment of the rigid tab 28 to the base plate, to accommodate a patient's anatomy 48 and/or corresponding medical/procedural requirements.

FIG. 2 details a side perspective view of a medical guidance device 10, with a force exerted on the device 10, mimicking real-world use of a medical guidance device 10. A force $F_n$ is exerted on the needle guide 24 and/or needle 32, which is representative of possible external forces applied by a medical personnel when using the device 10. As depicted, the force $F_n$ is opposed by the forces $F_{n1}$ and $F_{n2}$, applied by a first rigid tabs 28. The force $F_n$ is about equal to the combined forces $F_{n1}$ and $F_{n2}$ ($F_n=F_{n1}+F_{n2}$), thus resisting any movement in the medical guidance device 10 and ensuring accurate and consistent application of the needle 32 to and through the patient's anatomy 48. As seen in FIG. 2, two rigid tabs 28 are attached to the patient's anatomy 48, and demonstrate various degrees to rotation in the hinge joint 30, to allow for adequate adhesion to the patient's anatomy 48. In addition, FIG. 2 further includes a base plate adhesive 26 to further securing the device 10 to the patient's anatomy 48.

As provided in FIG. 3, the flexibility of the hinge joint 30 may be accomplished by a reduction of the material used for the rigid tab 28, about the horizontal axis "B" with respect to the base plate 12, thus creating the hinge joint 3o. Additional methods for creating the hinge joint 30 may include other mechanical hinges, including but not limited to, a saddle joint, pivot joint, ball and socket, condyloid joint, and other uniaxial and/or restricted multiaxial joints. Further depicted in FIG. 3 is the fitment of the ring frame 14 configured upon the base plate 12, as well as the attachment point of the rigid tab 28 to the base plate 12.

Figure 4:
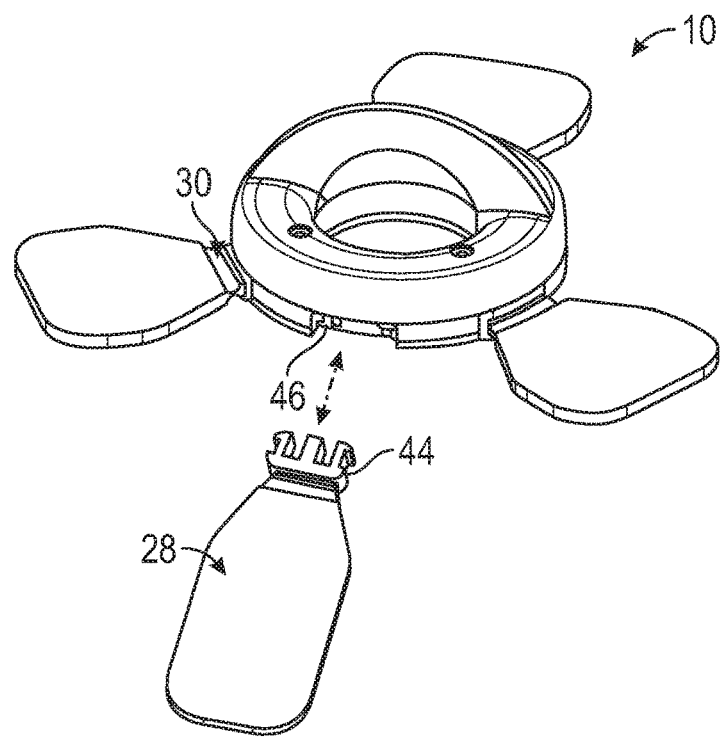
FIG. 4 illustrates a top perspective view of a medical guidance device, according to one or more embodiments of the present subject matter.
Figure 5:
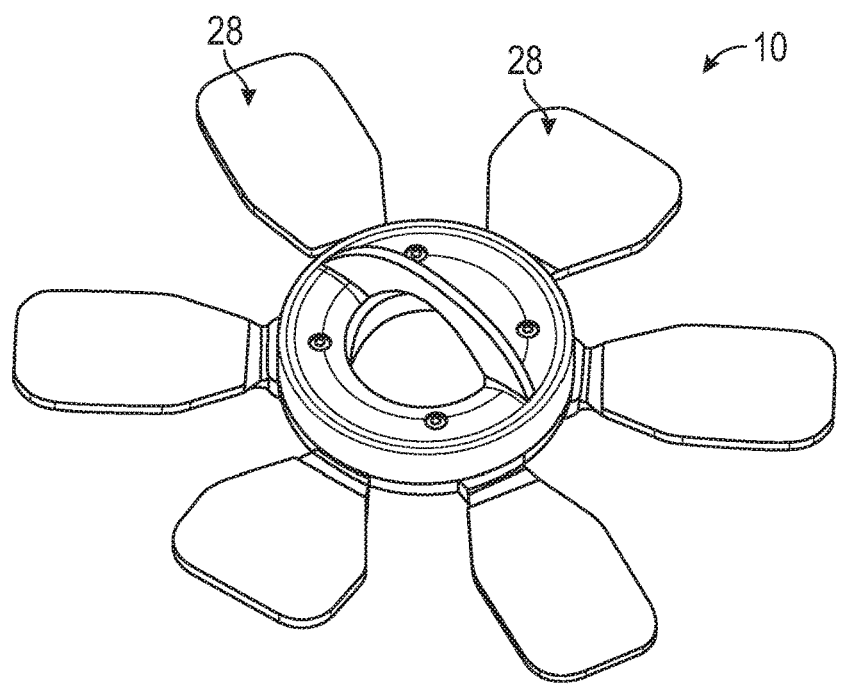
FIG. 5 provides a top perspective view of a medical guidance device, according to one or more embodiments of the present subject matter.

FIG. 4 illustrates a top perspective view of a medical guidance device 10 with the removable rigid tabs 28. As depicted, the rigid tab 28 comprises a clasp 44 at one end of the rigid tab 28, wherein the clasp 44 may be removably matted to the cavity 46 found on the base plate 12. As seen in FIG. 5, the rigid tab 28 may be configured in a variety of shapes to accommodate specific fitment upon the patient's anatomy and/or the requirements for medical/surgical procedure.

Figure 6:
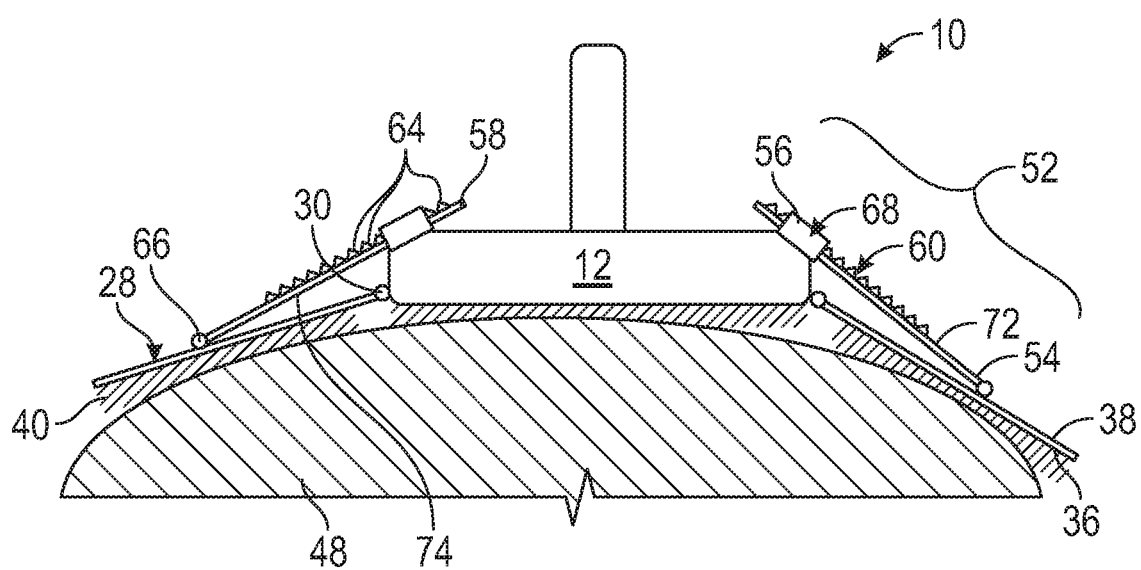
FIG. 6 illustrates a side perspective view of a medical guidance device, according to one or more embodiments of the present subject matter.
Figure 7:
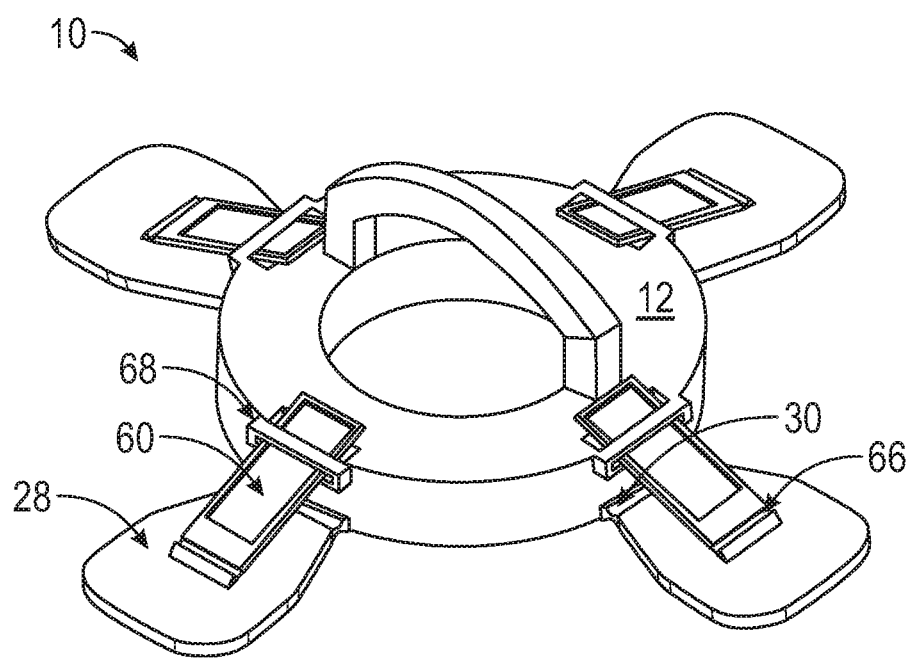
FIG. 7 displays a top perspective view of a medical guidance device, according to one or more embodiments of the present subject matter.
Figure 8:
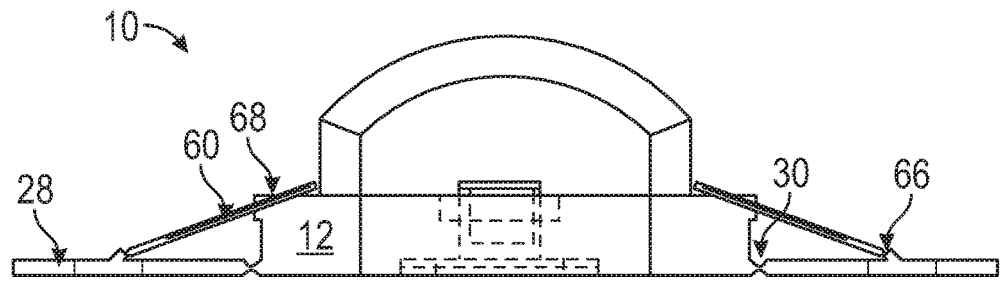
FIG. 8 is a side perspective view of a medical guidance device, according to one or more embodiments of the present subject matter.

FIGS. 6, 7 and 8 illustrate various perspective views of a medical guidance device 10 further incorporating a support member 52 in communication with the rigid tab 28 at a distal end 54 of the support member 52, and in communication with the base plate 12 at a proximal end 56 of the support member 52. The support member 52 is configured to increase support and rigidity of the rigid tab 28 with respect to the base plate 12, while allowing the rigid tab 28 to rotate about the horizontal axis "B" with respect to the base plate 12. Additional support and rigidity of the rigid tab 28 is accomplished by triangulation, as depicted in FIGS. 6 and 8. This triangulation effect is advantageous in resisting tip/tilt manipulation/motion of the medical guidance device 10, thus greatly enhancing the durability and accuracy of the device 10.

The support member 52 comprises a sliding fastener 58, and receiver 68 having a fissure 70 (not shown), wherein the fissure 70 is configured to accept and slideably retain the sliding fastener 58. In the embodiment provided in FIG. 6, the distal end 54 of the sliding fastener 58 is hingedly fixed to the rigid tab 28 by a sliding fastener hinge 66, allowing the sliding fastener 58 to rotate in the same plane as the hinge joint 30 found on the corresponding rigid tab 28. The proximal end 56 of the sliding fastener 58 is sliding fastened to the receiver 68 through the fissure 7o, wherein the receiver 68 is mounted to the base plate 12. The dorsal side 72 of the sliding fastener 58 includes a gear rack 60 which is configured to engage with a ratchet 62 (not shown) configured in the receiver 68. The teeth 64 of the gear rack 60 slidingly contact the ratchet 62, as the rigid tab 28 is rotated about the horizontal axis "B" with respect to the base plate 12, and the sliding fastener 58 is driven through the receiver 68. The teeth 64 and ratchet 62 may be configured to allow for the rigid tab 28 to only slide in one direction. In addition, the ratchet 62 may be configured to allow for disengagement of the ratchet 62 from the teeth 64, allowing the rigid tab 28 to be reset and/or reoriented.

Alternatively, the gear rack 60 may be configured on the ventral side 74 of the sliding fastener 58 for engagement with a ratchet 62 configured in the receiver 68. In various other embodiments, the proximal end 56 of the support member 52 may be hingedly fixed to the rigid tab 28, allowing the support member 52 to rotate in the same plane as the hinge joint 30 found on the corresponding rigid tab 28. The distal end 54 of the support member 52 is then sliding fastened to the sliding fastener 58, which is mounted to the rigid tab 28.

Furthermore, the sliding fastener 58 may incorporate alternative locking-adjustment mechanisms in place of the gear rack 60 and ratchet assembly 62, including, but not limited to, a screw, bolt/nut assembly, clamp, clips, retaining rings, threaded fastener, rubber band, and other fastening devices know in the art.

Similar to the hinge joint 30 utilized in the rigid tab 28, the distal end 54 of the support member 52 is hingedly fixed to the rigid tab 28 by a sliding fastener hinge 66. The sliding fastener hinge 66 allows the support member 52 to rotate in the same plane as the hinge joint 30 found on the corresponding rigid tab 28, thus further restricting movement of the rigid tab 28 with respect to the base plate 12. In further unison with the hinge joint 30, the sliding fastener hinge 66 may achieve flexibility about the horizontal axis "B" with respect to the base plate 12, by utilizing a mechanical hinge, including but not limited to, a saddle joint, pivot joint, ball and socket, condyloid joint, and other uniaxial and/or restricted multiaxial joints.

In addition, the receiver 68 may also be hingedly attached to the base plate 12 or rigid tab 28 (depending on configuration) thus allowing for optimal angle orientation of the receiver 68 as the rigid tab 28 is position (up and down) with respect to the fixed position of the base plate 12.

Figure 9:
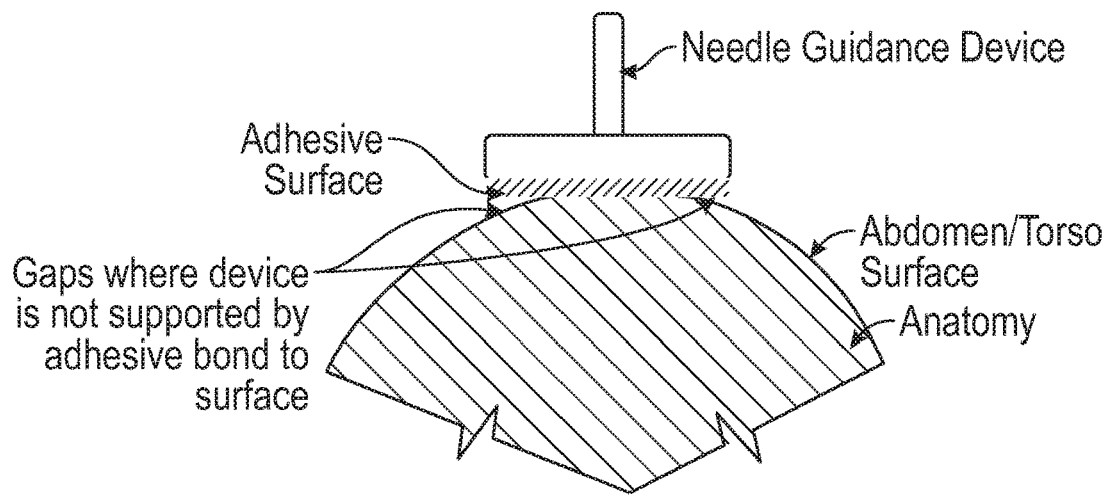
FIG. 9 illustrates a side perspective view of a medical guidance device mounted to a subject.
Figure 10:
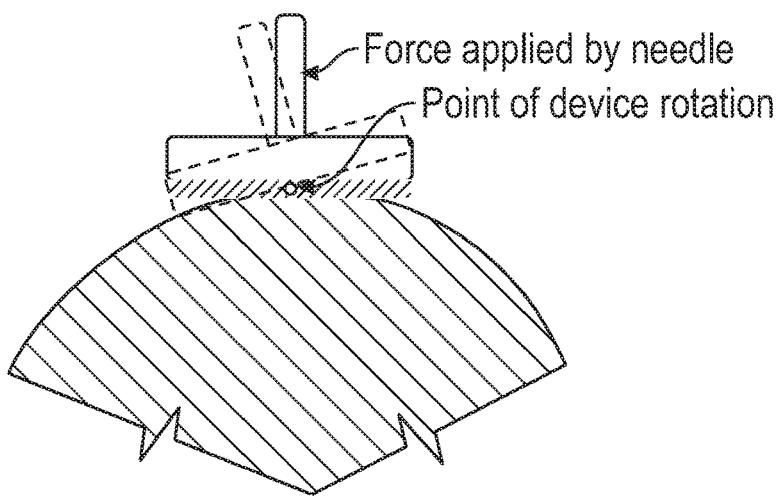
FIG. 10 provides a side perspective view of a medical guidance device mounted to a subject, with external force applied to the device.

FIGS. 9 and 10 illustrate side perspective views of a medical guidance device mounted to a patient's anatomy. These images provide the common instruments used in the art, as well as the associated rotation of the instrument when force is applied. As seen in FIG. 9, the instrument 100 is attached to the patient 102 via an adhesive surface. In the instant figure, the attachment point to the patient 102 is curved, leading to gaps 104 where the instrument 100 does not contact the patient 102. As further provided in FIG. 10, when force Fc is applied to the instrument 100, the instrument 100 is moved, compromising the stability of the instrument 100, as well as the efficacy of treatment and accuracy of the needle placement and advancement in to the patient.

The present application hereby incorporates by reference, in their entirety, U.S. patent application Ser. No. 13/837,806 for a "Needle Placement Manipulator with Two Rotary Guides", and Ser. No. 15/808,703 for a "Medical Guidance Apparatus".

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A medical guiding device comprising:
a base configured to guide a medical device; and
at least three tabs each releasable attached to the base and each extending distally from the base,
wherein the base is configured to allow for adjustment of the medical device to a desired angle with respect to a patient's anatomy;
wherein each of the at least three tabs are configured to attach to the patient's anatomy, anatomy, and each of the at least three tabs are rotatable in a single axis; and,
a support member is configured between the base and at least one of the at least three tabs such that the support member supports the at least one of the at least three tabs in the single axis.

2. The medical guidance device according to claim 1, wherein the axis of rotation of any one of the at least three tabs is in the axial direction with respect to the base.

3. The medical guidance device according to claim 1, wherein the base is configured to removably accept and reconfigure additional tabs.

4. The medical guidance device according to claim 1, wherein an adhesive for each of at least three tabs is configured to remove attached to the patient's anatomy.

5. The medical guidance device according to claim 1, wherein each of at least three tabs is reconfigurable in shape and size.

6. The medical guidance device according to claim 1, further comprising an adhesive on the base that is configured to remove attaching the base to the patient's anatomy.

7. The medical guidance device according to claim 1, wherein the support member further comprises a releasable locking-adjustment mechanism.

8. The medical guidance device according to claim 1, wherein the support member is hingedly attached to one of the at least three tabs near the second end of the support member.

* * * * *